United States Patent [19]

Wenk

[11] 4,408,601
[45] Oct. 11, 1983

[54] BONE COMPRESSION PLATE

[75] Inventor: Rolf A. Wenk, Balsthal, Switzerland

[73] Assignee: Wilh, Wenk AG, Hägendorf, Switzerland

[21] Appl. No.: 251,872

[22] Filed: Apr. 6, 1981

[30] Foreign Application Priority Data

Apr. 14, 1980 [CH] Switzerland .................. 2870/80

[51] Int. Cl.³ .............................. A61F 5/04
[52] U.S. Cl. .................. 128/92 D; 128/92 B
[58] Field of Search ............. 128/92 D, 92 R, 92 B, 128/92 C

[56] References Cited

U.S. PATENT DOCUMENTS

| Re. 28,841 | 6/1976 | Allgower et al. | 128/92 D |
|---|---|---|---|
| 3,528,085 | 9/1970 | Reynolds | 128/92 D |
| 3,552,389 | 1/1971 | Allgower et al. | 128/92 D |
| 3,716,050 | 2/1973 | Johnston | 128/92 D |
| 3,741,205 | 6/1973 | Markolf et al. | 128/92 D |
| 3,779,240 | 12/1973 | Kondo | 128/92 D |
| 4,219,015 | 8/1980 | Steinemann | 128/92 D |

Primary Examiner—Kyle L. Howell
Assistant Examiner—C. W. Shedd
Attorney, Agent, or Firm—Browdy & Neimark

[57] ABSTRACT

A bone compression plate is provided with several sliding slits for countersunk bone screws having ball heads in the longitudinal dimension of the plate. Each sliding slit is countersunk in its end area opposite the fracture, the depth of which countersinking in the plate determines the final axial position of the screwhead. That depth is greater than that of the rest of the sliding slit. The bearing surface of the countersinking for the screwhead extends over an area which is included within an angle of more than 180°. It is thus possible, on the one hand, to move the plate with respect to the pieces of fractured bone to obtain a pressing together of the two pieces of bone when the bone screw has not been screwed tight. On the other hand, it is possible to fasten the plate immovably to one piece of the fractured bone by inserting a bone screw into the countersink slit. Pressing of the pieces of bone fragment together can be accomplished automatically by means of chamfering provided on the ball head of the countersunk bone screw in the area at the opposite end of the sliding slit. Deeper countersinking provided in the end area containing the original countersunk depression makes possible the positioning of the countersunk bone screw at an oblique angle.

2 Claims, 8 Drawing Figures

U.S. Patent     Oct. 11, 1983     4,408,601
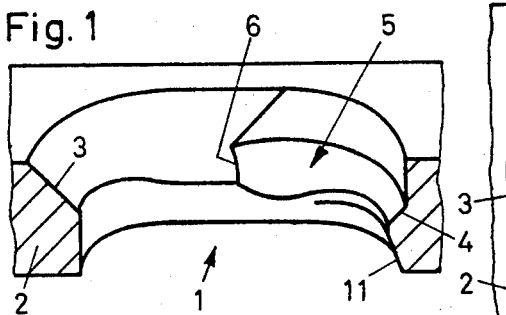
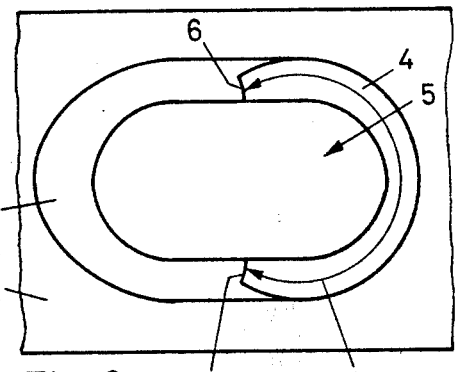
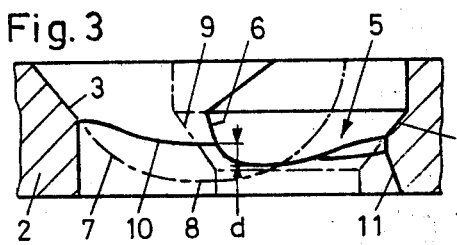
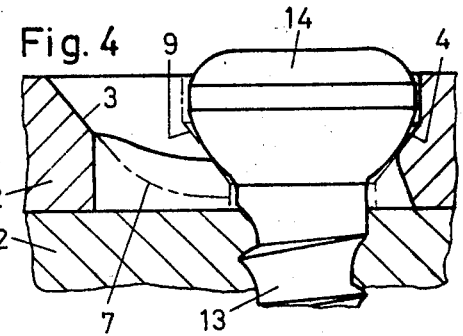
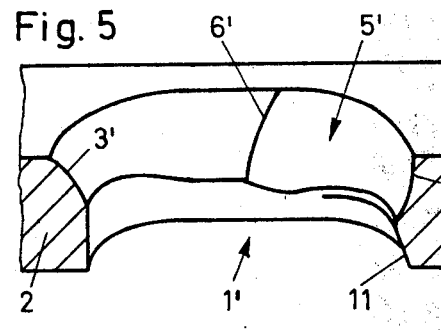
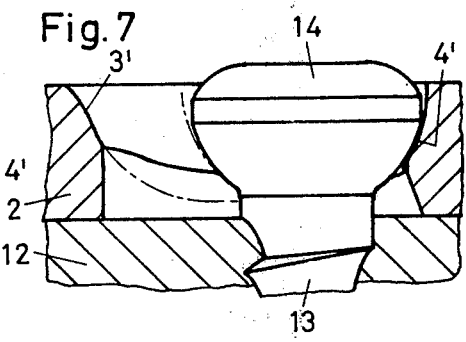
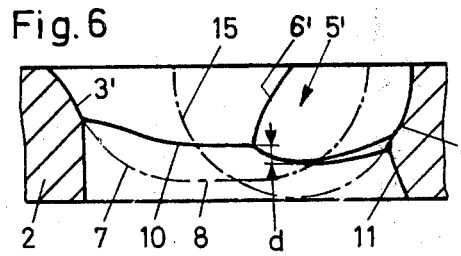
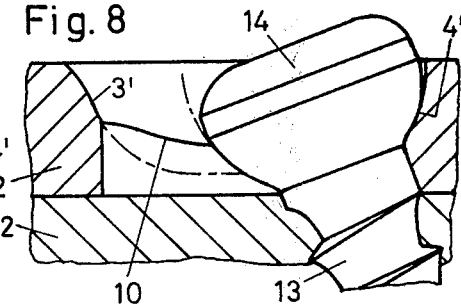

BONE COMPRESSION PLATE

BACKGROUND OF THE INVENTION

The invention is concerned with a bone compression plate. Such artificial bone compression or pressure plates used in osteosynthesis have either round holes formed with a spherical seat corresponding to the ball head of a screw or holes shaped like slits, which extend longitudinally along the plate and make a sliding movement of the plate possible. Screw holes which are countersunk for bone screws have been known for a long time and are used to ensure an osseous contact in the fracture area under compression. For the initial generation of pressure, that is, to press the two pieces of bone of the fracture together, a special clamping device, which is applied to the compression plate from the outside is used. This clamping plate is removed after the compression plate in contact with the pieces of fractured bone, has been screwed tight. In another embodiment, compression plates, in accordance with Swiss Pat. No. 462 375, are used. In this case, the countersunk holes (which correspond to the ball head of the screw as a horizontal half-cylinder and constitutes the seat for the screw) are provided in every sliding slit at the end of the slit, which is opposite the fracture. Chamfering is formed in the slit by a beveled half-cylinder which is inclined in such a way that when the screw head is sunk at that end of the sliding slit, the plate is, of necessity, pushed away from the location of the fracture in the longitudinal direction. If the plate is fastened by screws to the second of the two pieces of bone which are separated by the fracture, a longitudinal pushing of the fragment of the fracture, and consequently an automatic pressing of the two pieces of fractured bone against each other results from this longitudinal pushing of the plate. For the purpose of fastening the plate to the fractured bone, screws are sunk in a so-called neutral position in other slit-shaped holes in the plate to prevent a pulling apart of the fracture, that is, they are sunk at the place in the slit-shaped hole where the said inclined and horizontal half-cylinders run together.

In practice, both compression plates having round holes and those with slit-shaped holes, particularly those formed with chamfering to obtain the self-tightening effect which has been described above, are used. Depending upon the nature of the fracture, the surgeon will normally prefer a round-hole fastening having the advantage of a rigid connection between the screw, the bone and the plate and little necessary pressure of the plate on the bone. In other cases, he will use a sliding-slit fastening having the advantage of an automatic compression and the avoidance of any interference with the closing of the gap of the fracture. This choice will accept either the disadvantage of an interference effect in the case of round-hole fastening and a discontinuation of the compression, or even a pulling apart if the screw is placed eccentrically in the hole in the plate, in contrast with the disadvantage of a pulling apart in the case of a sliding-slit fastening if the screw is not placed precisely in the neutral position which could result in a loosening of the screw in the course of time.

To be able to use either screw holes of round or slit-shaped design, as desired, for optimum immobilization of the area of the fracture, compression plates of both kinds must therefore be available. Aside from the increased expense connected with this method, the application of the compression plate is unnecessarily made more difficult in many cases if the surgeon can only decide the most advantageous configuration of holes at the time of the insertion of the screws or, respectively, the pre-drilling of the bone part after bending the plate conformingly.

Making some of the screw holes in the compression plate slitlike in shape and others round, so that the compression plate is immovably fastened to the pieces of fractured bone after the final process of screwing the countersunk bone screws into the round holes is, in fact, known from Swiss Pat. No. 515 032. However, such compression plates incur the disadvantage that they are not universally usable any more because, depending upon the nature of the pieces of bone and the fracture, the slitlike holes and likewise the round holes have to be located at different places along the compression plate.

It is the object of the present invention to provide a compression plate of the type mentioned above, which contains exclusively slit-like holes for the corresponding countersunk ball-headed bone screws, but which makes possible an immovable fixing of the plate in the manner of screws of the round-hole type.

As explained below by means of exemplary embodiments of the present invention, with the aid of the drawings, the compression plate, according to the present invention, combines the advantages of plates with round as well as slit-like holes, avoids their disadvantages to a large degree and, additionally, has the important advantage of universal application with the possibility of being manufactured in a single model with no additional cost, with the exception that differing dimensions in length and width of the plate, necessarily and obviously, will be required.

BRIEF DESCRIPTION OF THE DRAWINGS

FIG. 1 shows, in perspective, a cross section of a compression plate, cut along its middle line, with a sliding slit having chamfering at one end of the slit and a tapered, rather deep, countersinking at the other end.

FIG. 2 shows a plan view of the upper surface of the cross section of the compression plate shown in FIG. 1.

FIG. 3 shows a longitudinal section through the sliding slit of FIG. 1, showing the lines to be followed by tools in producing the chamfering and the countersinking features of FIG. 1 mentioned above.

FIG. 4 shows a longitudinal section through the sliding slit of FIG. 1 with a completely countersunk bone screw holding the compression plate.

FIG. 5 shows a view, in perspective, corresponding to FIG. 1, but provided with a spherical countersinking of the sliding slit.

FIG. 6 shows a longitudinal section through the sliding slit of FIG. 5, showing lines to be followed by tools in producing the chamfering and the countersinking features of FIG. 5.

FIG. 7 shows a longitudinal section through the sliding slit of FIG. 5 with a completely countersunk bone screw holding the compression plate in place.

FIG. 8 shows a longitudinal section, as in FIG. 7, with a countersunk bone screw which has been countersunk at an oblique angle to the compression plate.

DESCRIPTION OF PREFERRED EMBODIMENT

FIG. 1 illustrates in perspective, a sliding or longitudinal slit 1 of a section cut along with middle line of a bone compression plate 2. Plate 2 is provided with several sliding slits running, in a known manner, longitudinally through the plate on both sides of the middle of it or offset alternately with respect to its middle line. The sliding slit, which is shown, is intended to receive a bone screw having a spherical bearing surface and, also in a known manner (cf Swiss Pat. No. 462 375), has a chamfering 3 at one end, that is, at the end away from the fracture. The chamfering 3 serves, as was described above, to tighten the bone screw which is partially screwed into one of the two pieces of bone which are to be pressed against each other. This displaces the plate 2 which is fastened to the other piece of bone in the longitudinal direction with respect to the piece of bone in question and, in that way, functions to press the two pieces of bone against each other without the use of any external clamping devices. In FIG. 2, sliding slit 1 of FIG. 1 is represented in plan view.

At its other end, which is the one opposite the fracture, the sliding slit 1 has a tapered bearing and limit-stop surface 4 which, in contrast with the limit-stop surfaces of the sliding slits known from the Swiss Pat. No. 462 375, for example, is provided with tapered countersinking 5 which is lower than the area of contact for the bone screw in the middle part of the sliding slit 1. Consequently, the bearing surface of the bone screw contacts an area which is included within an angle of more than 180° around the circumference. In FIG. 1, the edge of the slit 1 together with its middle part forms the tapered countersinking 5 which is represented as the line 6. Thus, the bearing surface 4 extends over an area b included within an angle of more than 180° between the two lines or edges 6, as can be seen in FIG. 2.

The producing and shaping of the sliding slit, depicted in FIG. 1, and particularly its countersinking 5, with the bearing surface 4, can be explained by reference to the longitudinal section shown in FIG. 3. The oblong hole opening of the sliding slit is first milled out using a cylinder milling cutter. Then the chamfering 3, which is straight in cross section, is milled out of the plate 2 to a certain depth 8, utilizing a slanting thrust of the tool, by means of a spherical cutter, which is indicated by a dot-dash line 7. Next, the spherical cutter is thrust horizontally over a short stretch, shown to the right in FIG. 3, and is then removed. Finally, the countersinking 5 of FIG. 1, provided with the bearing surface 4, is produced using a countersinking milling cutter, which is indicated by a dot-dash line 9. As can be seen from the boundary lines of the chamfering 3, which are shown in perspective in FIG. 1 and from the front in FIG. 3, the middle part of the sliding slit, along the line 10, which follows them and the bearing surface 4 of the countersinking 5, which closes off the sliding slit, the bearing surface of the countersinking 5 is deeper than the bearing surface in the middle part of the sliding slit by a distance d. A lower countersinking 11 is provided to make possible the positioning of a bone screw in the countersinking 5 at an oblique angle, as is explained in greater detail in the illustration of FIG. 8.

In FIG. 4, a bone screw 13 provided with a spherical head 14, which is completely countersunk in the countersinking 5 and screwed into the piece of bone 12, is shown. Good immobilization of the fracture with a mimimum amount of pressure exacted by the plate 2 on the piece of bone 12 is obtained using this embodiment when compared with that attained using plates provided with round holes. Other possible uses and advantages of plates possessing the sliding slit, as shown in FIGS. 1 through 4, will be described below, referring to the illustrations in FIGS. 5 through 8.

In FIG. 5, another embodiment of the sliding or longitudinal, slit 1 of the compression plate 2 is shown in perspective, in which the end opposite the fracture has a spherical bearing and limit-stop surface 4' which is formed with tapered countersinking 5'. The countersinking 5' also is formed deeper than the areas of contact for the bone screw in the middle part of the sliding slit 1'; consequently it embraces the bearing surface of the bone screw over an area included within an angle of more than 180° around the circumference, similar to that shown in FIG. 2 for the tapered countersinking 5. In FIG. 5, the edge which forms the tapered countersinking 5' with the middle part of the sliding slit 1' is represented as the line 6'.

The producing and shaping of the sliding slit 1' of FIG. 5 is shown in FIG. 6 in the same way shown in FIG. 3, the opening of the sliding slit first being milled out using a cylinder milling cutter. Then chamfering 3', which is curved concavely in cross section, is milled out of the plate 2 to a certain depth 8, again using a variably slanting thrust of the tool, by means of a spherical cutter which is indicated by a dot-dash line 7. Next the spherical cutter is thrust horizontally over a short stretch, to the right in FIG. 5, and is then removed. Finally, the countersinking 5' is milled out by exercising a vertical thrust with the same spherical cutter, which is indicated by a dot-dash line 15 at a point which is displaced horizontally. The bearing surface 4' is produced by that means and in this manner. As can be seen from the boundary line 10 of the bearing surface, in the middle part of the sliding slit 1', and the horizontal section of the bearing surface 4' in FIG. 6, the bearing surface 4' of the countersinking 5' is deeper than the bearing surface for the bone screw, which is indicated by the line 10 in the middle part by a certain distance. Once again, a lower chamfering of the countersinking 5' is designated by the numeral 11.

The curved chamfering 3', shown in FIGS. 5 and 6, results in a change in the longitudinal force along the line of compression, that is, the line along which the plate 2 moves as a result of the countersinking of the bone screw, which is required for a specific pull on the part of the plate 2. This pull is naturally constant in the case of the straight chamfering 3 of FIGS. 1 and 3. Because of the concave chamfering 3' of FIGS. 5 and 6, the required longitudinal force of the bone screw is at first greater than that of the embodiment in FIGS. 1 and 3, but this force becomes smaller than that of FIGS. 1 and 3 as the compression travel increases. However, since the plate 2 must exercise less pull when compression begins than at the end of compression, the embodiment possessing the chamfering 3' shown in FIGS. 5 and 6 in which a high pulling power of the plate 2 can be produced with relatively little longitudinal force being exerted by the bone screw.

In FIG. 7, the bone screw 13 having a spherical head 14, which is completely countersunk in the countersinking 5' and screwed into the piece of bone 12, is shown in the same way as is shown in FIG. 4.

Other details for using the disclosed compression plate embodiments are as follows. It has been mentioned above that the bone screw 13 can be sunk into the piece of fractured bone 12 through the sliding slit 1 or 1', in a known manner, in such a way that, when the screw is screwed in, its ball head 14 slides along the half-cylindrical or curved chamfering 3 or 3' and then rests on the half-cylindrical bearing surface indicated by the line 10 (FIGS. 3 and 6). As a result, the plate 2 is moved to the left with respect to the piece of bone 12 and by that means pulls the other piece of bone (not shown) to the piece of bone 12 to close the gap of the fracture. If that movement to close the gap of the fracture, which is known to be approximately 1 mm, is not enough, an aftercompression can be produced in another sliding slit in the same way. For the final fastening of the plate 2 to the piece of bone 12, a bone screw is not put into the so-called neutral position, that is, at the place where the half-cylinder of the chamfering 3 or 3' and the horizontal half-cylinder (Line 10) run together, in another sliding slit 1 or 1', but is placed in the countersinking 5 or 5' as shown in FIGS. 4 and 7. As a result, a good immobilization of the pieces of fractured bone is obtained with the exertion of minimum pressure.

This same compression plate 2 can be used by the surgeon during the operation if it seems desirable in view of the conditions of the fracture. However, a round-hole plate can also be used in the same way, using an external clamping device, which is subsequently removed. This clamping device is again used to press the pieces of bone together, the screws being inserted into the countersinkings 5 or 5' to fasten the plate. Furthermore, the compression plate described permits the practice of a sliding fastening process taking advantage of the function of the sliding slit 1 or 1'. Final fastening is accomplished by means of screws which are introduced into the countersinkings 5 or 5', even if an external clamping device is preliminarily used until the pieces of bone are definitively secured in an immobile position.

When a bone screw 13 is inserted in the tapered countersinking 5' near the fracture, a drawing apart of the fracture can be prevented automatically by taking into consideration normal manufacturing tolerances for the spherical screw head 14 and the tapered countersinking 5'. For this purpose, the screw is inserted eccentrically into the tapered countersinking 5' of FIGS. 5 and 6, in the sliding slit heading in a direction away from the fracture, utilizing a drilled jig which fits into the countersinking 5'. As a result, minimal compression in the direction of the fracture, and consequently maintenance of the static compression stress of the bone corticalis, can be achieved.

As can be seen from FIG. 8, there is the additional possibility of obtaining a universal positioning of the screw at an oblique angle by introducing the screw 13 centrally into the spherical countersinking 5' of the plate 2 which is provided with the lower chamfering 11.

The advantage of this procedure is that a supporting or self-tightening functioning is obtained and that the point of the screw avoids an area of a fracture involving the bone fragments.

Thus, the present invention provides a compression plate which is uniformly furnished with holes of the same kind, that is, the sliding slits 1 or 1' which have been described above. This leaves the surgeon free to chose whether or not to use every hole as a sliding slit and/or fastening hole in the same way as is done with a countersunk round hole. Furthermore, the construction of the compression plate, in accordance with the invention, does not result in an increase in the cost of production since the countersinking feature which has been described can be produced in the same working operation, as heretofore, i.e., on a numerically-controlled milling machine, for example.

What is claimed is:

1. An elongated bone compression plate having a longitudinal centerline and a transverse centerline, said plate being formed with a plurality of slitlike holes each adapted to receive a countersunk bone screw having a ball head, each said slitlike hole being located in said plate substantially along the longitudinal centerline thereof and on both sides of the transverse centerline thereof with one end of said slitlike holes being distal thereto, each said slitlike hole being a compound countersink and having a portion of substantially uniform depth forming a first countersunk depression extending from said one end of said slitlike hole and having a tapered second countersunk depression extending from its other end, the depth of said second countersunk depression being greater than the depth of said first countersunk depression, a bearing surface formed in said second depression cooperating with said ball head of a said bone screw, said bearing surface being formed in the area of said other end of said slitlike hole, and said bearing surface being provided over an angular zone which is symmetrical with respect to said longitudinal centerline and extending in total over an angle of more than 180° when seen in the plane defined by said longitudinal and transverse centerlines.

2. Compression plate as claimed in claim 1, wherein the countersunk slitlike hole at the end area of the compression plate has a chamfered end surface running longitudinally thus making possible the oblique positioning of the countersunk bone screw within the countersunk slitlike hole.

* * * * *